(12) United States Patent
Ho

(10) Patent No.: US 10,143,834 B2
(45) Date of Patent: Dec. 4, 2018

(54) ELECTROTHERAPEUTIC SOLE AND METHOD FOR MAKING THE SAME

(71) Applicant: Hoi Ming Michael Ho, Ontario (CA)

(72) Inventor: Hoi Ming Michael Ho, Ontario (CA)

( * ) Notice: Subject to any disclaimer, the term of this patent is extended or adjusted under 35 U.S.C. 154(b) by 1 day.

(21) Appl. No.: 15/590,041

(22) Filed: May 9, 2017

(65) Prior Publication Data
US 2018/0296821 A1    Oct. 18, 2018

(30) Foreign Application Priority Data

Apr. 13, 2017    (TW) .............................. 106112340 A

(51) Int. Cl.
| | |
|---|---|
| *A61N 1/00* | (2006.01) |
| *A61N 1/04* | (2006.01) |
| *A61H 39/00* | (2006.01) |
| *A61H 39/04* | (2006.01) |
| *A61N 1/36* | (2006.01) |

(52) U.S. Cl.
CPC ......... *A61N 1/0476* (2013.01); *A61H 39/002* (2013.01); *A61H 39/04* (2013.01); *A61N 1/0456* (2013.01); *A61H 2205/125* (2013.01); *A61N 1/36021* (2013.01)

(58) Field of Classification Search
CPC ........ A61N 1/04–1/0496; A61N 1/322; A61N 1/36; A61N 1/36021; A61H 39/002; A61H 39/04; A61H 2205/125
See application file for complete search history.

(56) References Cited

U.S. PATENT DOCUMENTS

| | | | | |
|---|---|---|---|---|
| 2006/0235465 A1* | 10/2006 | Koo | ..................... | A43B 1/0054 606/204 |
| 2009/0193680 A1* | 8/2009 | Pang | .................... | A43B 3/0005 36/43 |
| 2010/0318009 A1* | 12/2010 | Stanley | .................. | A61F 7/007 602/14 |
| 2013/0211296 A1* | 8/2013 | Chau | ........................ | A43B 1/00 601/17 |

* cited by examiner

*Primary Examiner* — Scott M. Getzow
(74) *Attorney, Agent, or Firm* — Bacon & Thomas, PLLC

(57) ABSTRACT

The present invention is to provide an electrotherapeutic sole and a method for making the same, wherein the electrotherapeutic sole is composed of nitrile-butadiene rubber (38%~42% by weight), conductive carbon black (37%~42% by weight), a softening oil (14%~17% by weight), a processing aid (3%~5% by weight), and an accelerant (1%~2% by weight) and has a top portion protrudingly provided with a plurality of electrode protuberances that correspond in positions to the acupoints in a human sole; the electrotherapeutic sole is also provided with a socket, thereby an electrotherapeutic pulse output terminal inserted into the socket can send the electrotherapeutic pulses generated by an electrotherapeutic pulse generator sequentially through the socket and the conductive carbon black in the electrotherapeutic sole to the tips of the electrode protuberances to massage the corresponding acupoints in the human sole.

8 Claims, 4 Drawing Sheets

US 10,143,834 B2

ELECTROTHERAPEUTIC SOLE AND METHOD FOR MAKING THE SAME

FIELD OF THE INVENTION

The present invention relates to an electrotherapeutic sole and a method for making the same. More particularly, the invention relates to an electrotherapeutic sole that is configured to connect with an electrotherapeutic pulse generator (e.g., a TENS/EMS device) and that does not require a complicated internal circuit in order to send the electrotherapeutic pulses generated by the electrotherapeutic pulse generator to the acupoints in the sole of a human foot.

BACKGROUND OF THE INVENTION

Acupoints, which constitute an important part of the Chinese meridian theories, refer to specific positions on the superficial meridians (i.e., pathways distributed in the human body to facilitate the circulation of life force, or qi, between body organs) that serve as confluences, relay stations, and entrances/exits of qi. When a person falls ill, the corresponding acupoints tend to have such pathological reactions as pain (when pressed), soreness, numbness, nodule formation, and/or swelling. A doctor, therefore, can diagnose a patient's disease according to the pathological reaction(s) taking place and may also treat the patient by stimulating the corresponding acupoints.

Conventionally, acupoints are stimulated by acupuncture or tui na. With the advancement of science and medicine, however, electrotherapy has been a major means of acupoint stimulation, given the fact that acupoints have proved to have low electrical resistance and high conductivity. For example, Dr. Richard Croon of Germany found a relationship between acupoints and the low-resistance points on the skin; Dr. Reinhold Voll, also of Germany, verified the existence of several low-resistance superficial channels in the human body that resemble the meridians in traditional Chinese medicine; and Dr. Yoshio Nakatani of Japan found a relationship between acupoints and ryodoraku, a specific form of acupuncture developed by the Japanese. Electrotherapy is a physical treatment involving electrical stimulation and is conducted as follows. To start with, electrode pads are attached to a patient's skin. Then, a series of current signals generated by an electrotherapeutic signal generator are sent through the electrode pads to the muscle groups under the skin to induce rhythmic yet involuntary partial contraction and relaxation of the muscle groups, thus stimulating the intended acupoints in a way similar to acupuncture.

Electrotherapy is non-invasive, non-pharmacological, and hence an ideal treatment for personal health maintenance at home. Transcutaneous electrical nerve stimulation (TENS) and electrical muscle stimulation (EMS), for instance, are two common methods of electrotherapy nowadays. TENS, which uses low-frequency pulse current to control pain, is based on the "gate control theory", according to which epidermal nerves (e.g., the Aβ nerve fibers) can be stimulated with weak low-frequency current to generate signals that turn off the "gate" of the corresponding sensory nerves (e.g., the Aδ nerve fibers and the C nerve fibers), thereby stopping the conduction of pain and producing a painkilling effect. EMS, on the other hand, causes muscle contraction and relaxation by stimulating the corresponding motor nerves so that passive physical exercise is carried out for the intended treatment or training. By adjusting the current frequency of the electrotherapeutic signals generated by a TENS or EMS device, therefore, simulated acupuncture can be achieved to stimulate the target acupoints.

However, the inventor of the present invention has found that most of the aforesaid electrotherapeutic instruments use electrode pads as the elements required for transmitting electrotherapeutic signals, and that each time electrotherapy is performed, each target acupoint has to be attached with one electrode pad because the electrode pads generally have a small surface area and must be adhesively and securely attached to all the intended acupoints respectively in order to produce the expected electrotherapeutic effect. Accordingly, multiple electrode pads are needed when it is desired to conduct electrotherapy on several acupoints at the same time, and the electrode pads must be respectively and adhesively attached to the acupoints before the electrotherapy begins so that all the acupoints can receive the therapy at once. It would be very inconvenient if electrotherapy is applied to a plurality of acupoints by turns. The sole of a human foot, for example, has many acupoints and includes reflex areas for almost all the organs in the body. It is common practice, therefore, to manually massage the acupoints in the soles, with a view to stimulating the reflex areas, promoting blood circulation through the body organs, discharging the wastes or toxins in the organs, and thereby enhancing metabolism. But if it is desired to stimulate the acupoints in the soles by electrotherapy instead of manual massage, the electrode pads cause problems. Since each electrode pad covers only a small area, and different parts of a human sole vary greatly in curvature, a large number of electrode pads must be used; nevertheless, it is difficult to firmly attach the electrode pads to all the intended acupoints respectively.

As a solution, shoe soles adapted for electrotherapy were developed, allowing a user's entire foot to stamp on such a sole. These soles are typically provided therein with additional electronic elements (e.g., conductive wires) or are coated with a conductive material such that the manufacturing process is exceedingly complicated. Moreover, when stamped on repeatedly for a long time, the electronic elements are prone to damage (e.g., the conductive wires may be broken), or the conductive material may peel off. In either case, the sole in question will lose its electrotherapeutic effect. Hence, the issue to be addressed by the present invention is to design a novel sole structure that not only has a simple production process, but also is structurally simple to ensure a lasting electrotherapeutic effect during long-term use.

BRIEF SUMMARY OF THE INVENTION

In light of the aforementioned drawbacks of the conventional electrotherapeutic soles, the inventor of the present invention incorporated years of practical experience in the industry into extensive research and repeated tests and finally succeeded in developing the electrotherapeutic sole disclosed herein and a method for making the same. The present invention is intended to provide a better electrotherapeutic sole that will be favored by the general public.

It is an objective of the present invention to provide an electrotherapeutic sole that includes a main body, a plurality of electrode protuberances, and a socket. The main body is a thin plate composed at least of nitrile-butadiene rubber (NBR) at a weight percentage of 38%~42%; conductive carbon black at a weight percentage of 37%~42%; a softening oil at a weight percentage of 14%~17%; a processing aid at a weight percentage of 3%~5%; and an accelerant at a weight percentage of 1%~2%. The electrode protuberances are integrally formed with the main body, are distributed over a top portion of the main body, and correspond in positions to the acupoints in a human sole so that when the human sole stamps on the top portion of the main body, the tips of the electrode protuberances are pressed against the corresponding acupoints in the human sole. The socket is provided in the main body. One end of the socket is electrically connected to the electrotherapeutic sole while the opposite end of the socket is formed with an insertion hole. Once inserted into the insertion hole, an electrotherapeutic pulse output terminal can send the electrotherapeutic pulses generated by an electrotherapeutic pulse generator sequentially through the socket, the conductive carbon black in the electrotherapeutic sole, and the tips of the electrode protuberances to the corresponding acupoints in the human sole. Thus, a user only has to stamp on the electrotherapeutic sole, and an acupoint-stimulating effect similar to that achieved by acupuncture will be produced. Moreover, the electrotherapeutic sole can conduct electric current effectively even after long-term use.

Another objective of the present invention is to provide a method for making an electrotherapeutic sole, wherein the electrotherapeutic sole is configured as described above. The method begins by mixing NBR, at a weight percentage of 38%~42%, thoroughly with conductive carbon black at a weight percentage of 37%~42%, a softening oil at a weight percentage of 14%~17%, a processing aid at a weight percentage of 3%~5%, and an accelerant at a weight percentage of 1%~2% to form a sheet. The sheet is then placed in the forming space of a forming mold and subjected to compression molding at a forming temperature of 171~189° C. for 199~221 seconds. Once the sheet cools down, the electrotherapeutic sole is completed. As the electrotherapeutic sole conducts electric current through the conductive carbon black, there is no need to install additional circuits, and this allows the conductive electrotherapeutic sole to be manufactured rapidly.

BRIEF DESCRIPTION OF THE SEVERAL VIEWS OF THE DRAWINGS

The objectives, technical features, and effects of the present invention can be better understood by referring to the following detailed description of some illustrative embodiments in conjunction with the accompanying drawings, in which.

DETAILED DESCRIPTION OF THE INVENTION

Figure 1:
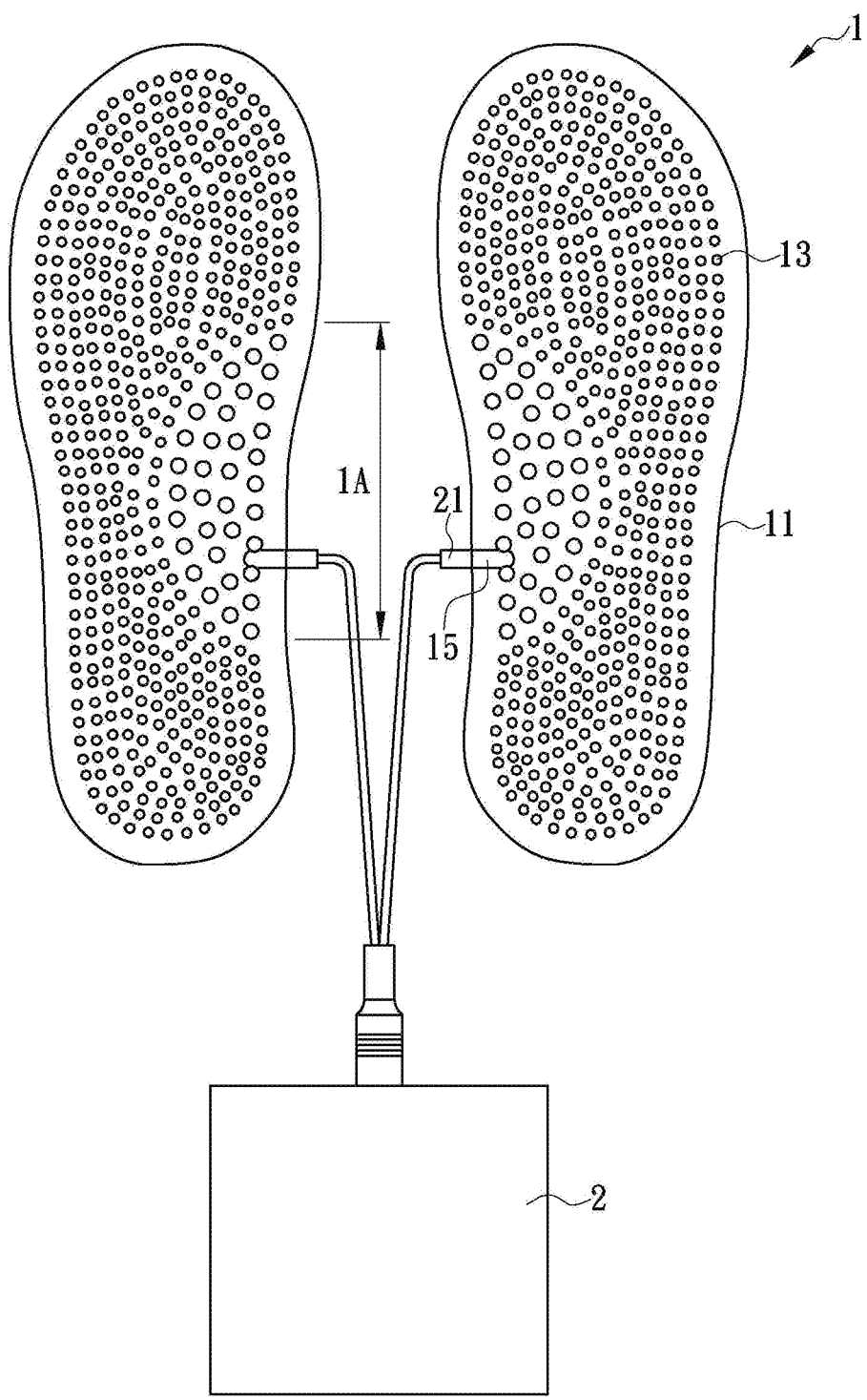
FIG. 1 is a top view of an electrotherapeutic sole according to the present invention.
Figure 2:
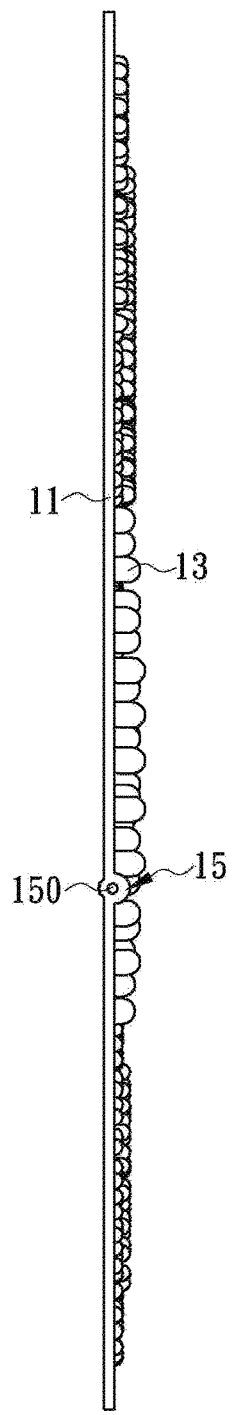
FIG. 2 is a side view of the electrotherapeutic sole in FIG. 1.

Referring to FIG. 1 and FIG. 2, the present invention provides an electrotherapeutic sole 1 and a method for making the same. The electrotherapeutic sole 1 can be used alone or placed in a piece of footwear (e.g., a slipper, sandal, aerobic shoe, or leather shoe) and is configured to be electrically connected to an electrotherapeutic pulse generator 2 (e.g., a TENS/EMS device). The electrotherapeutic sole 1 as shown in FIG. 1 and FIG. 2 is made of a mixture at least of nitrile-butadiene rubber (NBR), conductive carbon black, a softening oil, a processing aid, and an accelerant, wherein the NBR is at a weight percentage of 38%~42%; the conductive carbon black, 37%~42%; the softening oil, 14%~17%; the processing aid, 3%~5%; and the accelerant, 1%~2%. In other embodiments of the present invention, additional ingredients may be included to modify the properties (e.g., elasticity, hardness, and/or electrical conductivity) of the electrotherapeutic sole 1.

With continued reference to FIG. 1 and FIG. 2, the electrotherapeutic sole 1 includes a main body 11, a plurality of electrode protuberances 13, and a socket 15. The main body 11 is a thin plate having a thickness of about 1 mm. The electrode protuberances 13 are integrally formed with the main body 11 and are distributed over a top portion of the main body 11 in a way that corresponds to the way in which acupoints are distributed in a human sole. As most people's soles are not entirely flat but are concavely curved on the inner side (where the arch is), the electrode protuberances 13 in this embodiment vary in height, with those corresponding in position to the arch being the highest; consequently, the maximum thickness of the electrotherapeutic sole 1 reaches 4.5~6.5 mm (which is a combined height of the main body 11 and the electrode protuberances 13). The heights of the electrode protuberances 13 are so designed that when a user's sole stamps on the top portion of the main body 11, the tips of the electrode protuberances 13 are pressed against the corresponding acupoints in the user's sole.

As shown in FIG. 1 and FIG. 2, the socket 15 is provided in the main body 11 at a position corresponding to the arch of a human sole (i.e., the area indicated by 1A in FIG. 1). The socket 15 has one end electrically connected to the main body 11 and the opposite end formed with an insertion hole 150. The insertion hole 150 corresponds in position to a lateral edge of the main body 11 and is configured to be inserted by an electrotherapeutic pulse output terminal 21. As conductive carbon black is a semiconductor and has relatively low electrical resistance, the electrotherapeutic sole 1 is rendered conductive when conductive carbon black is evenly distributed in the electrotherapeutic sole 1. Once a user inserts the electrotherapeutic pulse output terminal 21 of the electrotherapeutic pulse generator 2 (e.g., a TENS/EMS device) into the insertion hole 150, stamps on the top portion of the electrotherapeutic sole 1, and turns on the electrotherapeutic pulse generator 2, the electrotherapeutic pulses generated by the electrotherapeutic pulse generator 2 will pass sequentially through the electrotherapeutic pulse output terminal 21, the socket 15, the conductive carbon black in the electrotherapeutic sole 1, and the tips of the electrode protuberances 13 to the corresponding acupoints in the user's sole, thereby stimulating, or massaging, the acupoints. It should be pointed out that while the socket 15 in this embodiment is integrally formed with the main body 11 and corresponds in position to the arch of the human sole, it is feasible in other embodiments of the present invention to design the socket 15 as a separate unit to be placed at an arbitrary position in the main body 11, and the position of the insertion hole 150 may also be adjusted according to design requirements, provided that the socket 15 has one end connected to the main body 11 and the opposite end formed with the insertion hole 150 for electrical connection with the corresponding electrotherapeutic pulse output terminal 21.

Figure 3:
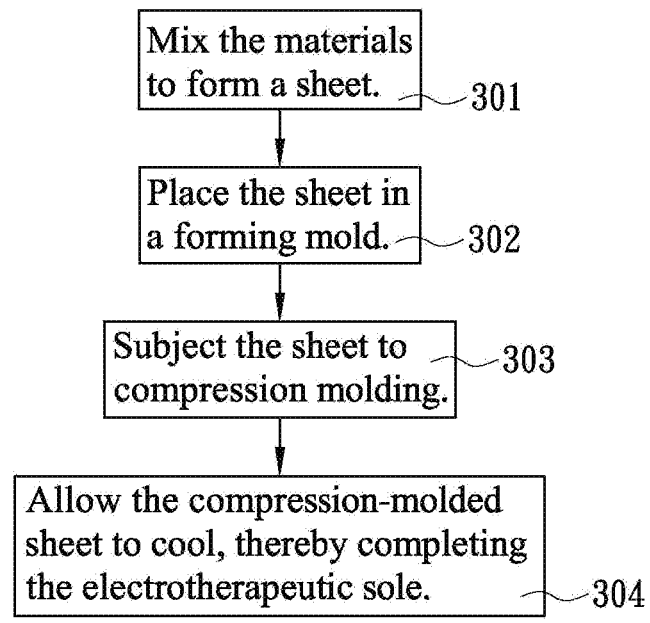
FIG. 3 is the flowchart of the manufacturing process of the present invention.
Figure 4:
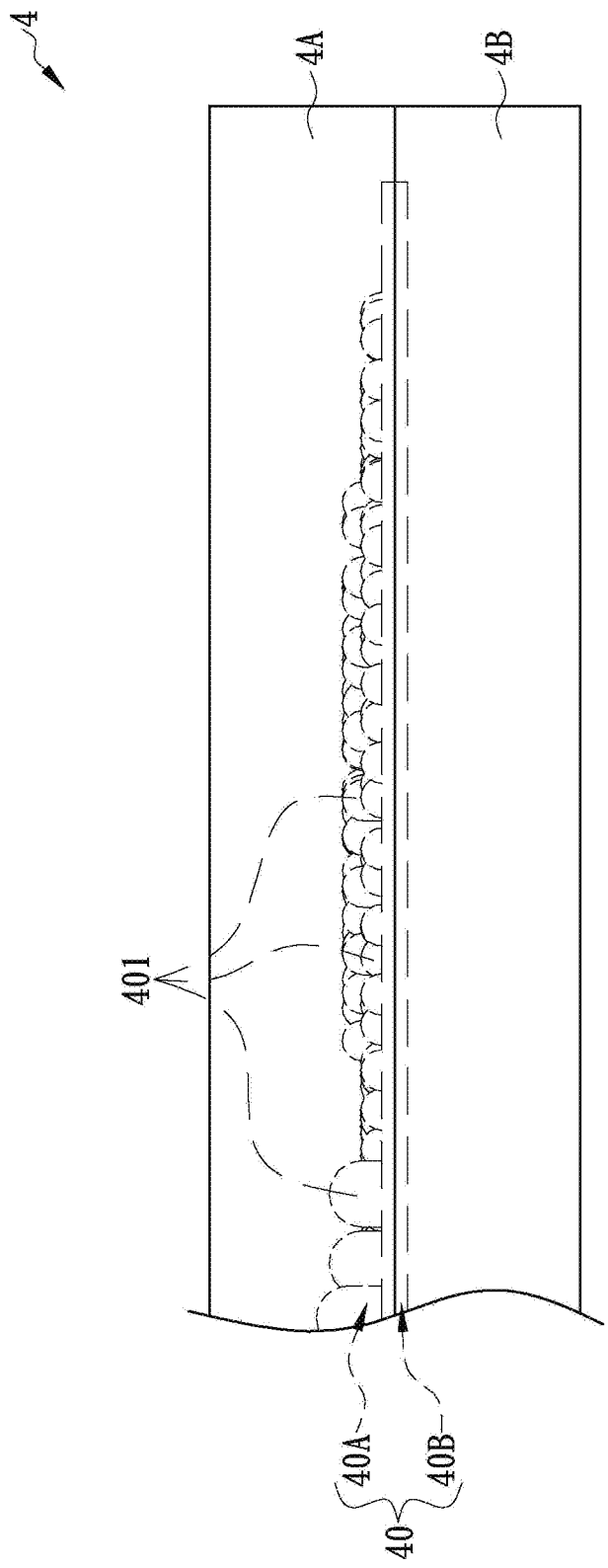
FIG. 4 schematically shows a forming mold for use in the present invention.

The method for making the electrotherapeutic sole 1 is detailed below with reference to FIGS. 1~3. First of all, the aforesaid materials (namely the NBR, the conductive carbon black, the softening oil, the processing aid, and the accelerant) are thoroughly mixed to form a sheet (step 301). The sheet in this embodiment has a hardness of 57~63° A (Shore A) and a thickness of 4.5~6.5 mm. After that, the sheet is placed in the forming space 40 of a forming mold 4 (step 302). As shown in FIG. 4, the forming mold 4 includes an upper mold 4A and a lower mold 4B, and the corresponding areas of the upper and lower molds 4A and 4B are each concavely provided with at least one sole-molding cavity 40A, 40B. The sole-molding cavities 40A and 40B form the forming space 40 when the upper mold 4A and the lower mold 4B are put together. In addition, the sole-molding cavity 40A of the upper mold 4A is concavely provided with a plurality of sunken portions 401, and the sole-molding cavity 40B of the lower mold 4B has a flat bottom wall. In other embodiments of the present invention, however, the constituent parts of the forming mold 4 may be modified and be different from those described above. The configuration of the sole-molding cavity 40B in the lower mold 4B may also be modified according to production or design requirements. For example, in cases where the bottom side of the electrotherapeutic sole 1 is required to be anti-slip, the sole-molding cavity 40B may have a wavy or other suitable configuration in order for the bottom side of the electrotherapeutic sole 1 to have the corresponding configuration.

Referring again to FIGS. 1~4, the sheet is subjected to compression molding by the forming mold 4 at a forming temperature of 171~189° C. for 199~221 seconds, or until the sheet takes the shape of the forming space 40 (step 303). After the compression molding process, the compression-molded sheet is allowed to cool to complete the electrotherapeutic sole 1 of the present invention (step 304). The electrotherapeutic sole 1 has a hardness of 57~63° A (Shore A) and a thickness of 4.5~6.5 mm. The electrode protuberances 13 are formed where the sheet corresponds to the sunken portions 401, and the bottom portion of the electrotherapeutic sole 1 has a flat surface due to the configuration of the sole-molding cavity 40B in the lower mold 4B. Besides, the socket 15 and the insertion hole 150 are automatically formed on the electrotherapeutic sole 1 thanks to the shape of the forming space 40 of the forming mold 4. Since different types of electrotherapeutic pulse output terminals 21 may vary in configuration (e.g., in length, it is feasible in other embodiments of the present invention to form the desired insertion hole 150, or more particularly to adjust the shape and depth of the insertion hole 150, by drilling the cooled compression-molded sheet as appropriate, in order for the corresponding electrotherapeutic pulse output terminal 21 to be securely inserted into the insertion hole 150 and send the electrotherapeutic pulses generated by the electrotherapeutic pulse generator 2 (e.g., a TENS/EMS device) through the socket 15 to the conductive carbon black in the electrotherapeutic sole 1 and then to the tip of each electrode protuberance 13. Now that the electrotherapeutic sole 1 depends on the conductive carbon black distributed therein, rather than additional electronic circuits conventionally required to be provided in the electrotherapeutic sole, as pathways of current conduction, the electrotherapeutic sole 1 is exempt from electronic component damage after long-term use, which damage, however, is typical of the conventional electrotherapeutic soles; in other words, the electrotherapeutic sole 1 of the present invention is expected to have a longer service life than its prior art counterparts.

While the invention herein disclosed has been described by means of specific embodiments, numerous modifications and variations could be made thereto by those skilled in the art without departing from the scope of the invention set forth in the claims.

What is claimed is:

1. An electrotherapeutic sole, comprising:
a main body formed as a thin plate and composed at least of nitrile-butadiene rubber (NBR), conductive carbon black, a softening oil, a processing aid, and an accelerant, wherein the NBR makes up 38%~42% by weight of the main body; the conductive carbon black, 37%~42%; the softening oil, 14%~17%; the processing aid, 3%~5%; and the accelerant, 1%~2%;
a plurality of electrode protuberances integrally formed with the main body, distributed over a top portion of the main body, and corresponding in position to acupoints in a human sole so that when the human sole stamps on the top portion of the main body, tips of the electrode protuberances are pressed against corresponding said acupoints in the human sole; and
a socket having an end electrically connected to the main body and an opposite second end formed with an insertion hole so that an electrotherapeutic pulse output terminal inserted into the insertion hole is able to send electrotherapeutic pulses generated by an electrotherapeutic pulse generator sequentially through the socket, the conductive carbon black in the electrotherapeutic sole, and the tips of the electrode protuberances to the corresponding acupoints in the human sole.

2. The electrotherapeutic sole of claim 1, wherein the electrotherapeutic sole has a hardness of 57~63° A.

3. The electrotherapeutic sole of claim 2, wherein the electrotherapeutic sole has a maximum thickness of 4.5~6.5 mm.

4. The electrotherapeutic sole of claim 3, wherein the electrotherapeutic sole has a bottom portion formed with a flat surface.

5. The electrotherapeutic sole of claim 2, wherein the socket is provided in the main body at a position corresponding to the arch of the human sole, and the second end of the socket is formed with the insertion hole at a position corresponding to a lateral edge of the main body.

6. The electrotherapeutic sole of claim 3, wherein the socket is provided in the main body at a position corresponding to the arch of the human sole, and the second end of the socket is formed with the insertion hole at a position corresponding to a lateral edge of the main body.

7. The electrotherapeutic sole of claim 4, wherein the socket is provided in the main body at a position corresponding to the arch of the human sole, and the second end of the socket is formed with the insertion hole at a position corresponding to a lateral edge of the main body.

8. The electrotherapeutic sole of claim 1, wherein the socket is provided in the main body at a position corresponding to the arch of the human sole, and the second end of the socket is formed with the insertion hole at a position corresponding to a lateral edge of the main body.

* * * * *